(12) United States Patent  
Gharib et al.

(10) Patent No.: US 6,717,172 B2
(45) Date of Patent: Apr. 6, 2004

(54) DIFFRACTIVE OPTICAL FLUID SHEAR STRESS SENSOR

(75) Inventors: Morteza Gharib, San Marino, CA (US); Daniel W. Wilson, Glendale, CA (US); Siamak Forouhar, Carlsbad, CA (US); Richard E. Muller, Altadena, CA (US); Dominique Fourguette, Pasadena, CA (US); Darius Modarress, Pasadena, CA (US); Frederic Taugwalder, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/025,218

(22) Filed: Dec. 18, 2001

(65) Prior Publication Data

US 2002/0162956 A1 Nov. 7, 2002

Related U.S. Application Data

(60) Provisional application No. 60/256,798, filed on Dec. 19, 2000.

(51) Int. Cl.[7] .............................................. G01N 21/49
(52) U.S. Cl. .......................... 250/574; 356/28; 356/441; 73/861

(58) Field of Search ........................... 250/550, 214 R, 250/216, 208.6, 221, 222.2, 237 G, 573–575; 356/27–28.5, 32, 35.5, 305, 336–338, 342–343, 436, 468, 441–442, 339, 520–521, 340; 340/619; 73/861

(56) References Cited

U.S. PATENT DOCUMENTS

| | | | |
|---|---|---|---|
| 3,216,318 A | | 11/1965 | Gaffard |
| 3,548,655 A | * | 12/1970 | Rudd ........................ 356/28.5 |
| 5,327,218 A | * | 7/1994 | Igaki ........................ 356/499 |
| 5,680,211 A | * | 10/1997 | Kaneda et al. ............... 356/499 |
| 5,701,172 A | * | 12/1997 | Azzazy ...................... 356/28 |
| 5,835,217 A | | 11/1998 | Medecki |
| 6,249,351 B1 | * | 6/2001 | de Groot .................... 356/512 |

* cited by examiner

*Primary Examiner*—David Porta
*Assistant Examiner*—Patrick J. Lee
(74) *Attorney, Agent, or Firm*—Fish & Richardson P.C.

(57) ABSTRACT

A diffractive optic sheer stress sensor operates by forming diverging fringes over a linear area of measurement. A diode laser focuses light onto a diffractive lens which focuses the light to respective slits. The slits form diverging fringes, and scattered light from the fringes is collected by a window and focused by another diffractive lens to a receiver.

53 Claims, 9 Drawing Sheets

X 10.000 μm/div
Z 2.000 μm/div

OVERALL PROTOTYPE SIZE:
Ø15x20mm

FIG. 8

150 MICRONS ABOVE SURFACE

FIG. 9A

50 MICRONS ABOVE SURFACE

FIG. 9B

SLITS

DIFFRACTIVE OPTICAL FLUID SHEAR STRESS SENSOR

CROSS-REFERENCE TO RELATED APPLICATIONS

This application claims benefit of U.S. Provisional Application No. 60/256,798, filed Dec. 19, 2000.

STATEMENT AS TO FEDERALLY-SPONSORED RESEARCH

The U.S. Government has certain rights in this invention pursuant to Grant No. N66001-99-1-8902 awarded by ONR.

BACKGROUND

A shear stress sensor may determine the shear stress of a fluid, e.g., in the area of an obstacle. Various shear stress sensors are known. These may be large and difficult-to-align devices.

SUMMARY

The present application teaches an integrated shear stress sensor which detects light scattering off particles flowing through a two-slit interference pattern. An embodiment uses diffractive optics in order to determine the shear stress.

BRIEF DESCRIPTION OF THE DRAWINGS

These and other aspects will now be described in detail with reference to the accompanying drawings, wherein.

DETAILED DESCRIPTION

Figure 1:
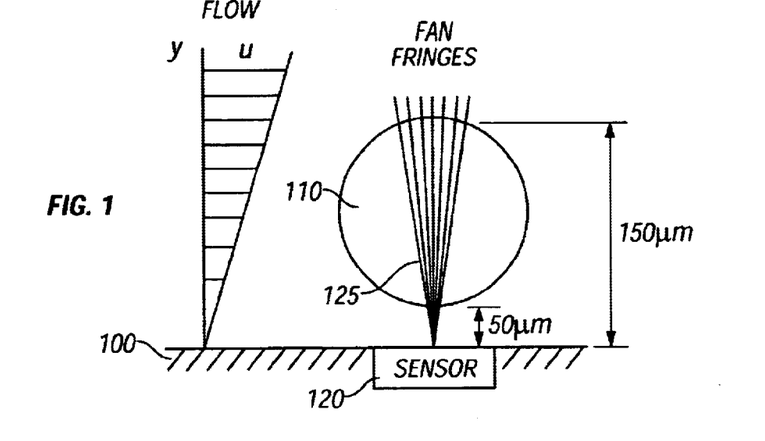
FIG. 1 shows a schematic of the principle used according to the embodiment, to determine the shear stress.

FIG. 1 shows a schematic illustrating the principle of the shear stress sensor. The sensor may operate to detect particle motion in a fluid. The sensors may determine the shear stress of the fluid in an area spaced from the wall 100, for example within a few hundred microns from the wall. The measurement area 110 in FIG. 1 is shown as a 100 micron diameter area beginning 50 microns from the wall and ending 150 microns from the wall. Within the measurement area 110, the velocity gradient may be considered as being substantially linear as $u=\delta y$, where u is the velocity, $\delta$ is the shear stress and y is the vertical coordinate.

A sensor assembly 120 is placed adjacent the wall. The sensor generates a linearly diverging fringe pattern 125 having a specified fringe spacing. The fringe spacing can be expressed as $$\Delta = Ky$$

where K is the slope of the first nonvertical fringe.

As particles in the fluid flow through the linearly diverging fringes, they scatter light to a detector. The light is scattered with a frequency f that is proportional to the velocity of the fluid flow, and inversely proportional to the fringe separation. Therefore, $$f = \alpha u/\Delta.$$

Considering the equations above, the measured frequency becomes inversely proportional to the wall shear as:

$$f = \frac{\sigma}{Ky} = \frac{1}{K}\sigma$$

The techniques described in Naqwi and Reynolds, "Dual Cylindrical Wave Laser-Doppler Method For Measurement Of Skin Friction In Fluid Flow" report No. TF-28, Stanford University (1987) has been demonstrated using conventional optics. A nonlinearity of the velocity profile or fringe pattern translates into widening and skewness of a resulting frequency distribution.

Figure 2:
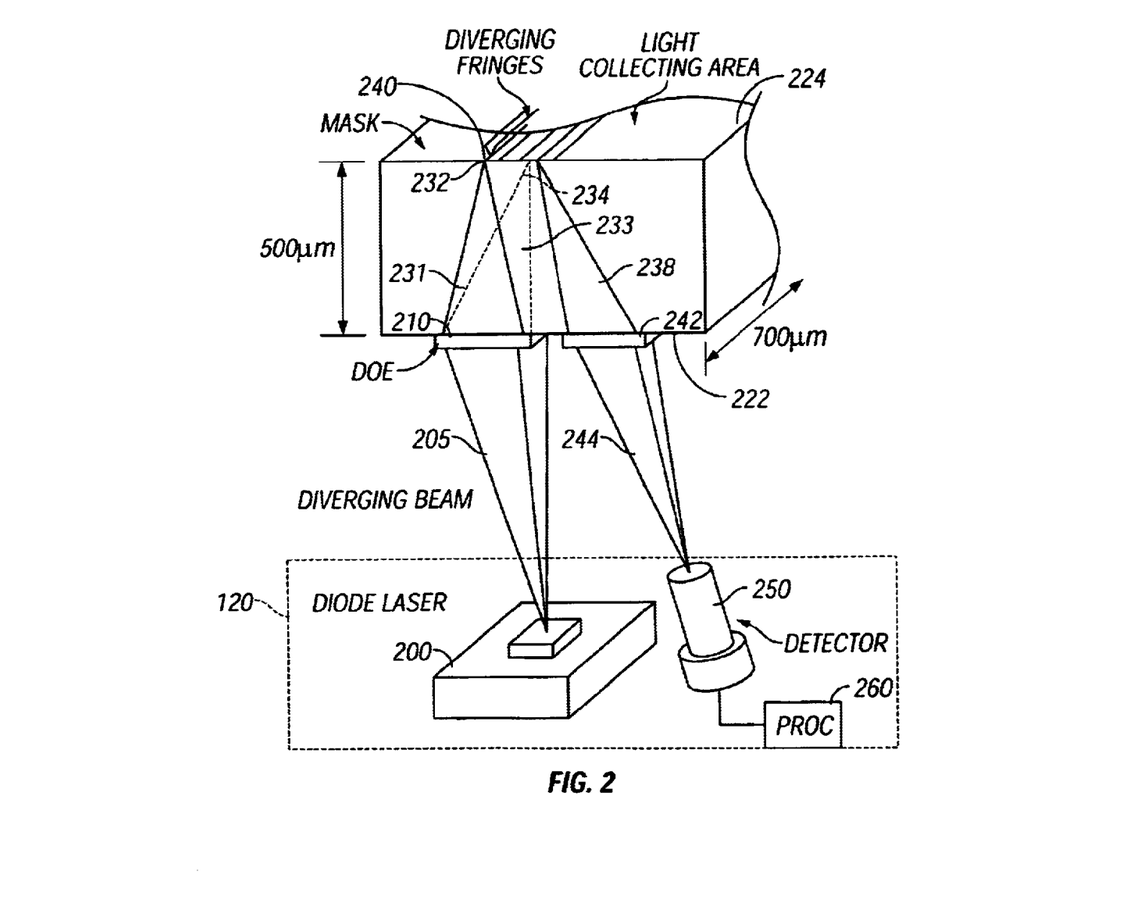
FIG. 2 shows an illustration of the sensor assembly of a first embodiment.

A detailed drawing of the sensor and its operation is shown in FIG. 2. The sensor 120 is formed of a diode laser 200 which produces a diverging beam 205 that is directed to an optical assembly formed from a quartz substrate 220. The quartz substrate is basically divided into a transmission part shown on the left in FIG. 2 and a collection part shown on the right in FIG. 2. A first surface 222 of the quartz substrate 220 has a diffractive optical element 210. The diffractive optical element focuses the diverging light to two parallel line foci as 231, 233. These foci may be coincident with two slits 232, 234 in a mask 240 which is located on the second, opposite surface 224 of the quartz substrate. The light diffracts from the slits 232, 234, and interferes. The interference forms an approximation of linearly diverging fringes. Fluid particles scatter the light traveling through the fringe pattern. This scattered light is collected through a window 236 in the metal mask. The window 236 is spaced from the slits 240 in a specified direction. The window directs the collected light 238 to a second diffractive optical element 242 which is also on the first surface 222. The second diffractive optical element 242 is spaced from the first diffractive element 210, also in the specified direction. This second diffractive optical element 242 may focus the light as 244 to a detector 250. The detector therefore receives information indicative of the particles being detected. This information may be coupled to a processor 260 which may process the information to determine information about sheer stress in the measurement area.

Figure 3A:
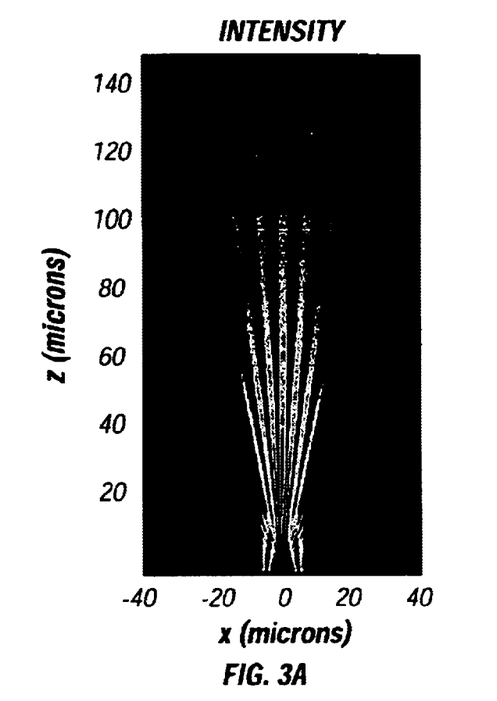
FIGS. 3a and 3b show an exemplary fringe pattern.
Figure 3B:
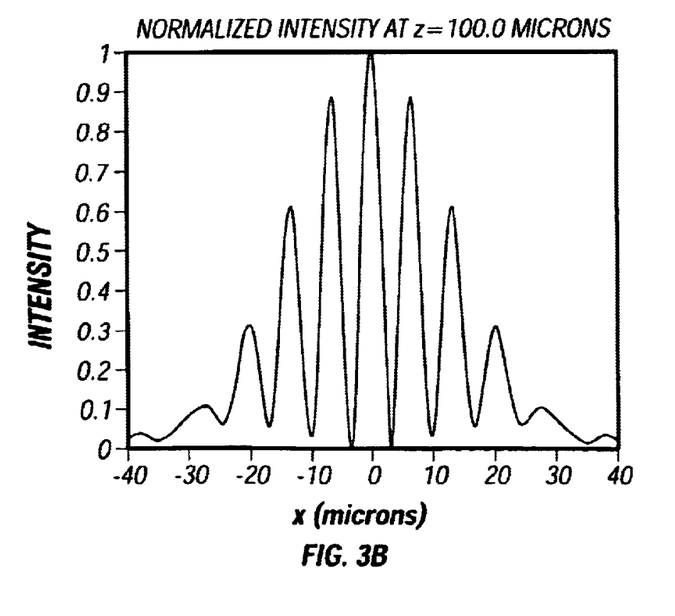

FIGS. 3A and 3B show a simulation of a finite-difference fringe pattern for slits that are 2 microns wide and separated by 10 microns. The fringe pattern displays a number of fringes which may be adequate for measurements. FIG. 3a shows the actual fringe pattern resulting from the two micron slits. FIG. 3b shows the normalized intensity of these fringes. The number of fringes may be determined by the slid width, and the divergence of the fringe pattern may be determined by slit separation.

Figure 4:
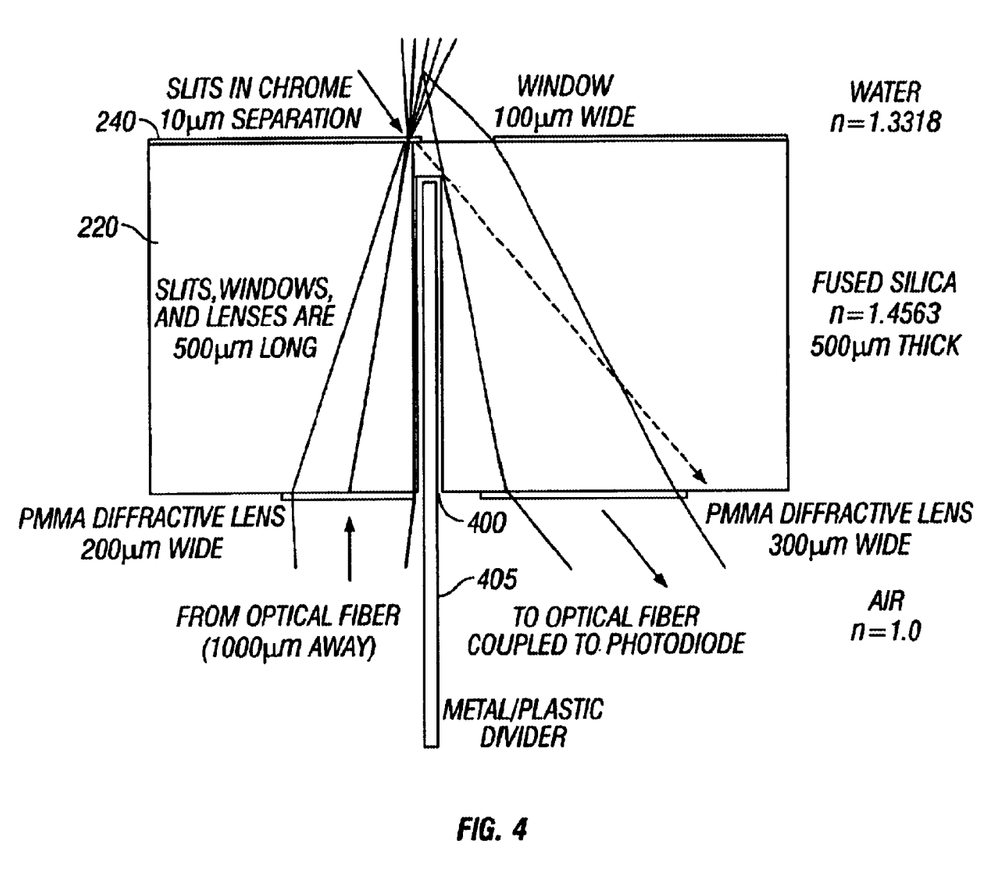
FIG. 4 shows a layout of the quartz substrate used for the sensing.

The formation of the sensor element may be carried out using two sided lithography on the quartz substrate 220. For example, the quartz substrate may be a 500 micron thick substrate having the dimensions shown in FIG. 4. The substrate 220 is covered with a chrome mask 240. The slits and the window are formed in the chrome mask. The slits 232, 234, and the window 236 may be formed by direct-write electron-beam lithography, followed by wet etching of the evaporated chrome.

The diffractive optical elements 210, 242 may be formed from polymethyl methacrylate (PMMA) that is located on the surface 222. The PMMA may be fabricated by an analog direct-write electron-beam lithography, followed by acetone development. The basic system of forming optical elements in this way is described in general in Maker, at al "Fabrication And Performance Of Optical Interconnect Analog Phase Holograms Made By E-Beam Lithography", Optical Electronic Interconnect And Packaging, Proceedings SPIE (1996)

Figure 5A:
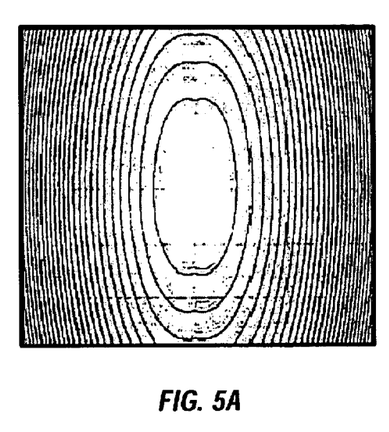
FIGS. 5a and 5b show a first embodiment of the fringes of the diffractive optical element.
Figure 5B:
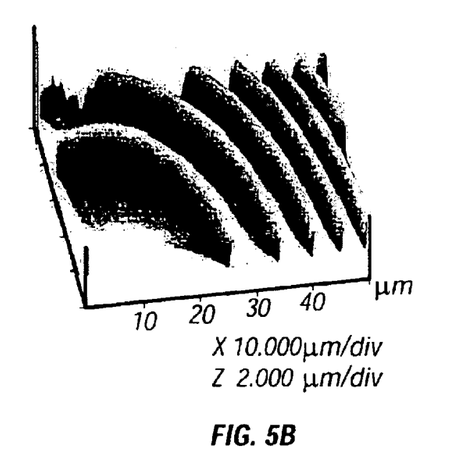

FIGS. 5A and 5B show two different diagrams of the dual line focus-laser DOE. The DOE collimates in a plane perpendicular to the drawing, and focuses to two lines that are substantially coincident with the slits 240, in a plane that is parallel to the drawing. The embodiment shown in FIGS. 5A and 5B may use the left half of the diffractive optical element to focus to the left slit and the right half of the diffractive optical element to focus to the right slit. This may operate reasonably well, but may also produce unequal illumination of the slits if the optical element is itself non-uniformly illuminated.

Figure 6:
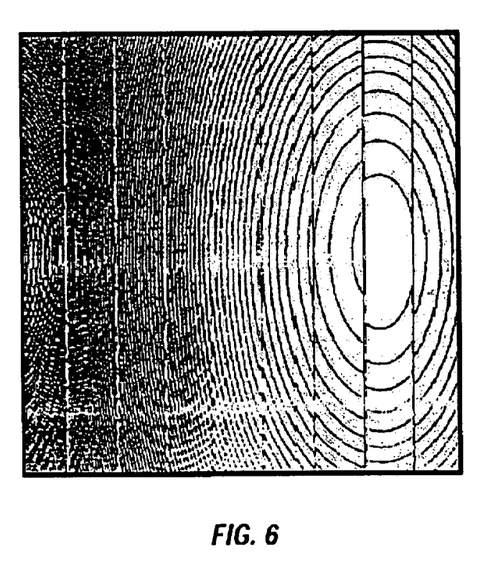
FIG. 6 shows a second embodiment of the diffractive optical element.

FIG. 6 shows a full aperture version of the dual line DOE. This lens combines a splitting grating phase function with a focusing lens phase function. In this way, both slits receive light from the full lens aperture, and both have equal illumination regardless of lens illumination.

Figure 7:
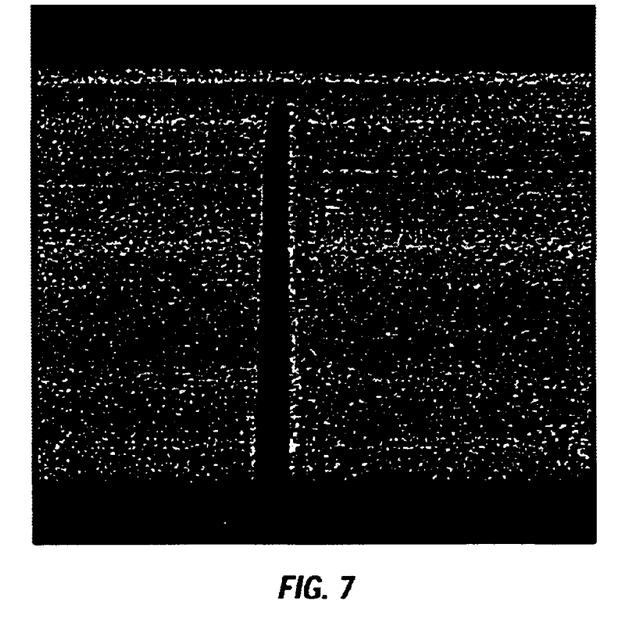
FIG. 7 shows a cross-sectional diagram of an isolation slot between the emitter and receiver.

After fabrication on both sides is complete, a slot may be cut between emitter and receiver lenses using a dicing saw. The slot 400 may be filled with an opaque material, or with an opaque divider such as 405. This may be used to optically isolate between the emitter portions and the receiver portions.

Figure 8:
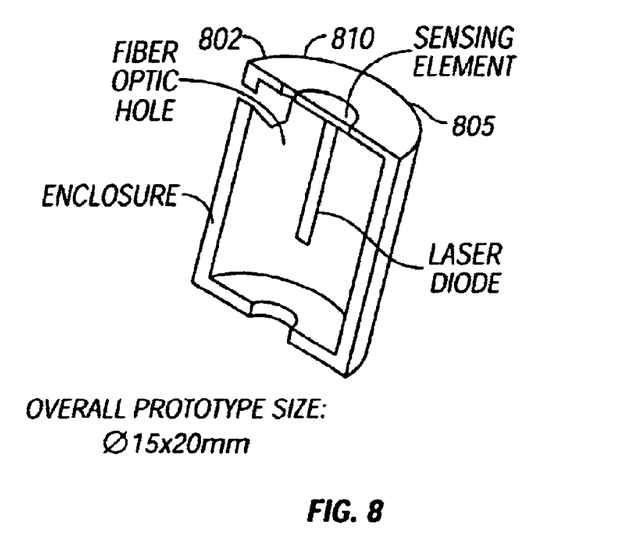
FIG. 8 shows the basic packaging system of the embodiment.
Figure 9A:
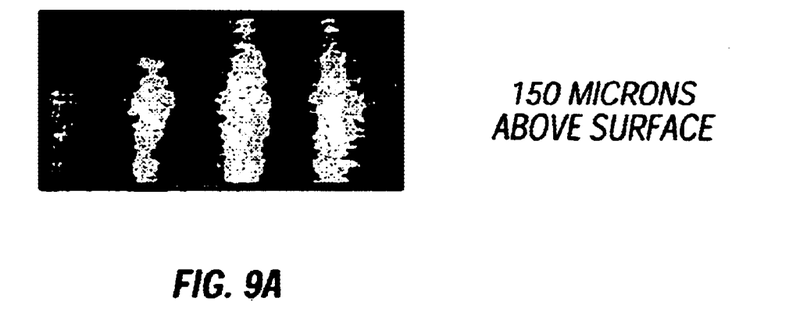
FIGS. 9A–9C show positions of the optical fringes at different heights above the surface of the element.
Figure 9B:
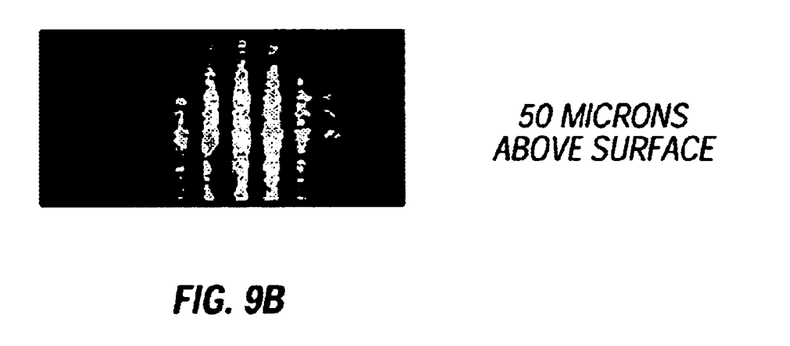
Figure 9C:
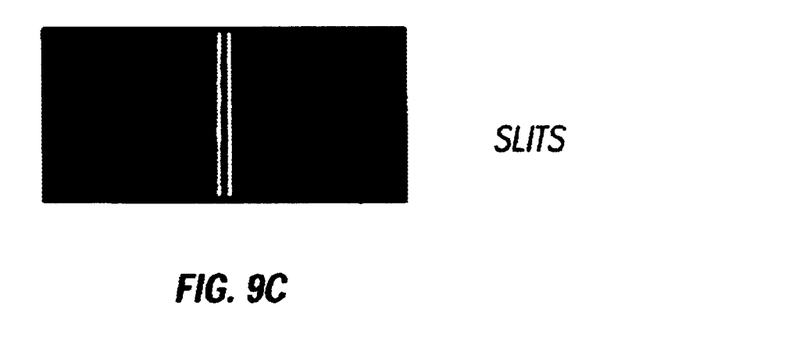

FIG. 8 shows a package containing all of the subject matter described above. A laser diode 802 is coupled to the package wall 805. The laser diode may be, for example, a 660 nm laser diode. A port 810 may contain the sensing element and receive the collection fiber. This device may be 15 mm in diameter and 20 mm in length. FIGS. 9A–9C shows fringe divergence with reference to the slits. The slits shown in FIG. 9C produce a fringe of FIG. 9B at 50 microns above the surface, and produce the pattern of FIG. 9A at 150 microns above the surface.

Figure 10:
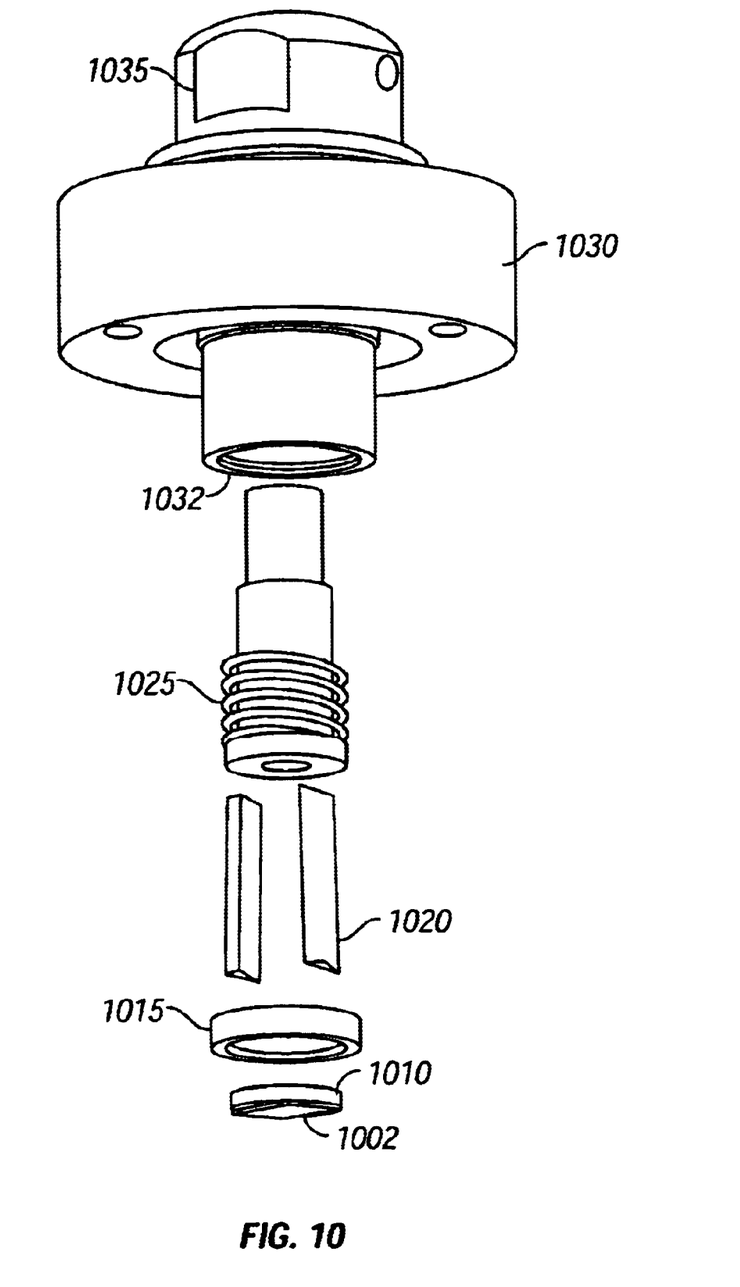
FIGS. 10 and 11 respectively show exploded and assembled views of this shear stress sensor assembly.
Figure 11:
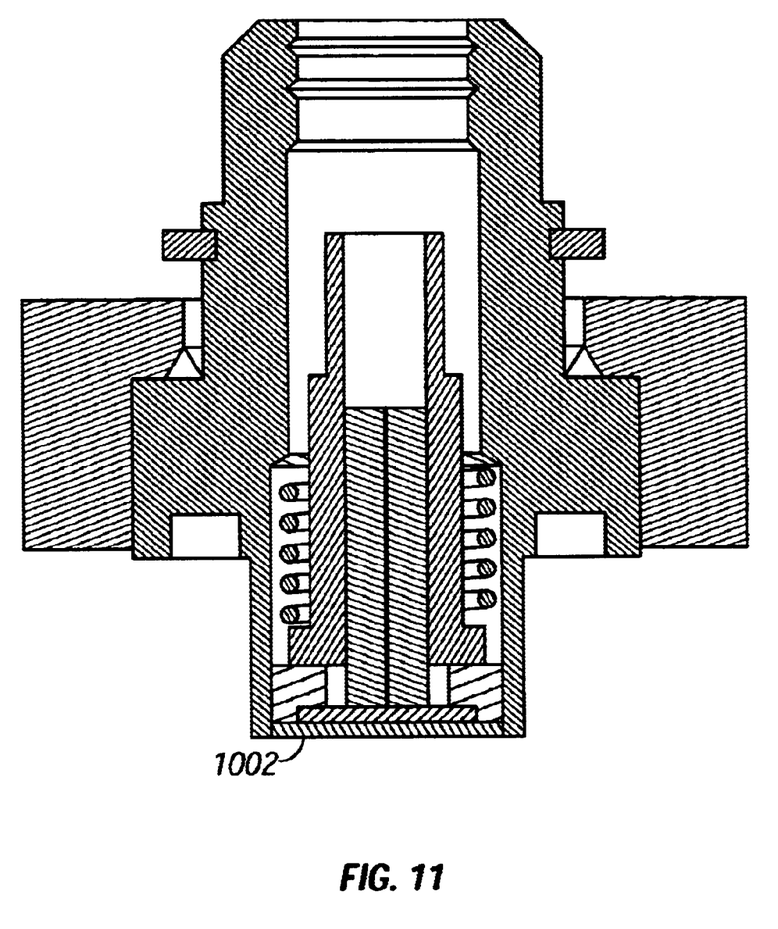

An alternative mechanical arrangement is shown in FIG. 10. In this embodiment, an integrated assembly is formed. The sensor 1002 is formed on a silicon spacer 1010 that is located in an assembly spacer 1015. The edges of the spacer 1010 fit within the inner surfaces of the assembly spacer 1015 which holds the chip rigidly into place. The assembled drawing is shown in FIG. 11 shows the chip 1002 being held in this way. A plurality of ferrules 1020 press against the rear surface 1015, and a spring 1025 presses the ferrule Holder. The entire assembly is held within a clamp 1030 which has an inner surface 1032 that holds the spring and ferrule assembly. The clamp 1030 also includes a retaining ring 1035 and other body parts.

The light is brought to the transmitter through the ferrules 1020, and also retrieved from the chip through the same ferrules. The ferrules may include fibers that are inserted in the ferrules which may themselves be formed of Zr. The ferrules may be held within a coupling part, as shown, that presses the ferrules into a defined registration orientation. Standard Zr ferrules may be ground to the proper size, and held in place using ultraviolet glue, in order to obtain the desired fiber spacing. The fibers may be included within the ferrules. Then, the ferrule/fiber assembly may be polished to obtain an optically clean assembly.

Figure 12:
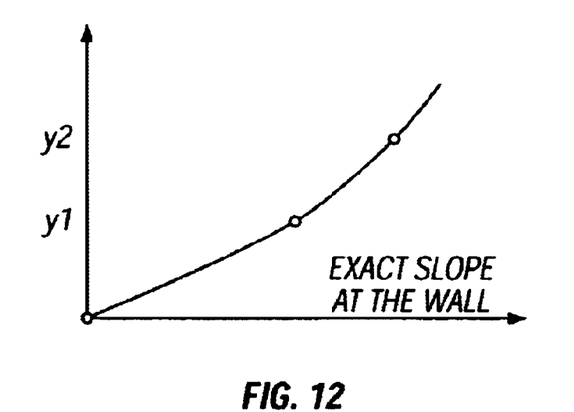
FIG. 12 shows a graph of the velocity measurements outside the viscous sublayer and their relations.

Another embodiment may use a two point measurement system in order to more accurately measure the wall stress and higher Reynolds numbers, e.g. Reynolds numbers higher than $10^6$. For higher Reynolds numbers, the linear velocity area of the viscous sublayer can be as thin as a few microns above the surface. FIG. 12 illustrates how a single point measurement may not provide an accurate measurement of the velocity gradient at the wall. However, this embodiment overcomes this issue by measuring the velocity at two points above the surface.

Figure 13:
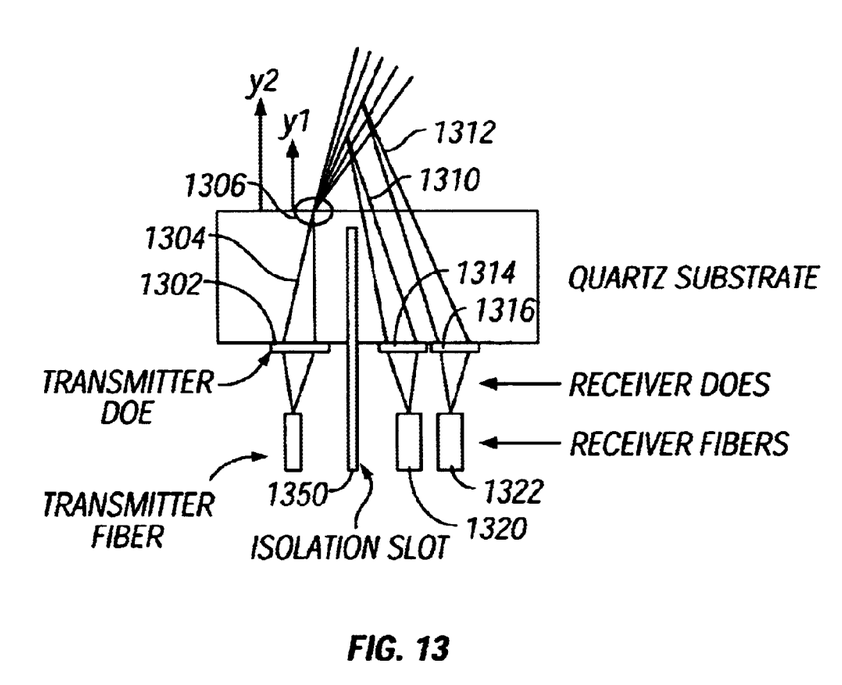
FIG. 13 shows a second embodiment for obtaining information from multiple velocity components.

The two points shown in FIG. 12 as y1 and y2 are measured. The so-called no-slip condition enables measuring the gradient at the wall by fitting a curve through these two points. A block diagram of this system is shown in FIG. 13. In this embodiment, the light is transmitted from either a diode laser or fiber 1300 as in the first embodiment to a diffractive optical element 1302. The light 1304 from the diffractive optical element is coupled through slits at 1306 and points from two different locations y1 and y2 are measured by the fringes. The locations of these two points are set by the windows 1310, 1312, and the incoming radiation is collected by receivers 1314, 1316. The collected light is focused into respective receiver fibers 1320, 1322. By measuring the information at the two points, and fitting a curve to these two points, more accurate information may be obtained. As in the other embodiments, an isolation slot 1350 may be provided. In this embodiment, the isolation slot may be filled with blue dye epoxy of the type known as P/N T60-065-B2. The lenses may be aligned with the spacer windows and attached using the blue dye epoxy.

Although only a few embodiments have been disclosed in detail above, other modifications are possible. All such modifications are intended to be encompassed within the following claims, in which:

What is claimed is:

1. An assembly, comprising:
 a source of illumination;
 an optical substrate, comprising:
   1) an illumination converting element, coupled to a first surface of said optical substrate, and which focuses said illumination to first and second foci;
   2) first and second slits, coupled to a second surface of said optical substrate and held in place relative to said optical substrate adjacent said first and second foci, and placed to cause said illumination to emit from said first and second slits and interfere to form linearly diverging fringes over a measurement area; and
   3 a light collecting part, coupled to a surface of said optical substrate, collecting light which is scattered from particles in said measurement area to determine information about said particles in said measurement area.

2. An assembly as in claim 1, further comprising a processing element, which processes information indicative of the light collected by said light collecting part to determine information related to shear stress.

3. An assembly as in claim 1, wherein said illumination converting element is a diffractive optical element.

4. An assembly as in claim 1, wherein said optical substrate having first and second opposite surfaces, wherein said first optical surface is closer to said source of illumination, and said second optical surface is more distant from said source of illumination and adjacent maid measurement area, said optical substrate being optically transparent.

5. An assembly as in claim 4, wherein said optical substrate is formed of quartz.

6. An assembly as in claim 4, wherein said illumination converting element is located on said first surface of said optical substrate, and maid first and second slits are located on said second surface of said optical substrate.

7. An assembly as in claim 4, wherein said second surface of said optical substrate has an optical mask formed thereon of an optically blocking substance, said optical mask including slits therein forming said first and second slits.

8. An assembly as in claim 7, wherein said optical mask also includes a light collecting window therein, spaced from said first and second slits, and positioned to receive scattered light from particles in said measurement area.

9. An assembly as in claim 8, further comprising a second illumination converting element, on said first surface of said optical substrate, and positioned to receive light from said light collecting window.

10. An assembly as in claim 9, wherein said second illumination converting element includes a diffractive optical element.

11. An assembly as in claim 9, wherein said light collecting part comprises an optical detector.

12. An assembly as in claim 1, wherein said slits include 2 micron wide slits which are separated by 10 microns.

13. An assembly as in claim 4, further comprising an optical divider, dividing said optical substrate and optically isolating between a transmitting part of said optical substrate and a receiving part of said optical substrate.

14. An assembly as in claim 13, wherein said optical divider comprises a notch formed in said optical substrate, and an optically opaque device formed in said notch.

15. An assembly as in claim 1, wherein said illumination converting element includes a diffractive lens formed of PMMA.

16. An assembly as in claim 1, wherein said illumination converting element comprises a portion which is used to focus to a first slit, and another portion which is used to focus to a second slit.

17. An assembly as in claim 1, wherein said illumination converting element provides illumination to areas of both of first said second slits from a full portion of the object aperture.

18. An assembly as in claim 1, wherein said source of illumination includes a diode laser.

19. An assembly as in claim 1, wherein said source of illumination includes a fiber carrying illumination.

20. An assembly as in claim 1, wherein said source of illumination includes a fiber within a ferrule.

21. An assembly as in claim 20, wherein maid ferrule is formed of Zr.

22. An assembly as in claim 1, wherein said light collecting part includes a light detector, and a second illumination converting element, which provides scattered light from said measurement area to said light detector.

23. An assembly as in claim 22, wherein said second illumination converting element includes two separated illumination converting element, each receiving scattered light from a different location.

24. An assembly as in claim 13, wherein maid optical divider is formed of a colored epoxy.

25. A sensor, comprising:
an optical substrate, having first and second opposite surfaces, a first surface formed with first and second diffractive lenses thereon, and a second surface formed with an optical mask having holes therein;
said first diffractive lens providing a collimation to two separate locations,
said optical mask having slits therein at said two separate locations of a type which are effective to create linearly diverging fringes over a measurement area;
said optical mask also including a window at a location which is spaced from said two separate locations, to receive light that is scattered from said measurement area,
said second diffractive lens spaced from said first diffractive lens in the same direction that said window is spaced from said slits, said second diffractive lens being operative to receive and collimate said scattered light from said window.

26. A sensor as in claim 25, further comprising a laser source, providing laser light to said first diffractive lens.

27. A sensor as in claim 26, wherein said laser source includes a laser diode.

28. A sensor as in claim 26, wherein said laser source includes an optical fiber.

29. A sensor as in claim 25, wherein maid second diffractive lens includes first and second separated diffractive lenses, spaced from one another, and obtaining information from two separate locations.

30. A sensor as in claim 25, wherein said optical substrate includes a notch therein, separating an transmission area of said first diffractive lens and said slits from an collection area of said second diffractive lens and said window.

31. A sensor as in claim 30, wherein said notch is filled with an optically opaque material to optically isolating between said transmission area and said collection area.

32. A sensor as in claim 31, wherein said optically opaque material is colored epoxy.

33. A sensor as in claim 26, further comprising an optical receiver, receiving light from said second diffractive lens.

34. A sensor as in claim 33, further comprising a processing element, processing an output indicative of said light from said second diffractive lens.

35. A sensor as in claim 25, wherein said first and second diffractive lenses are formed of PMMA.

36. A sensor, comprising;
an optical substrate, having a first area with a first optical element and a plurality of slits which in combination with said first optical element forms linearly diverging fringes over a measurement area, and having a second area with a receiving window for scattered light from said measurement area and a second optical element receiving said scattered light from said receiving window, said optical substrate including an optical isolator which isolates between said first area and said second area.

37. A sensor as in claim 36, wherein said optical substrate is formed of an optically transparent substance.

38. A sensor am in claim 37, further comprising a notch formed in said optically transparent substance, and an optically opaque substance in the notch.

39. A sensor as in claim 36, further comprising an optical source producing laser light to said first optical element.

40. A sensor as in claim 36, wherein said first and second optical elements are diffractive lenses.

41. A sensor as in claim 36, wherein said second optical element includes two separate optical elements receiving illumination from two separate locations.

42. A sensor as in claim 36, wherein there are two of said slits, and said first optical element directs separate foci to said two slits.

43. A sensor as in claim 42, wherein said first optical element includes a first portion which directs energy to one of said slits and a second portion which directs energy to another of said slits.

44. A sensor as in claim 42, wherein said first optical element uses an entire area of said element to direct energy to both of said slits.

45. A sheer stress sensor, comprising:

an optical substrate, having a first area with a first optical element and a plurality of slits which in combination with said first optical element forms linearly diverging fringes over a measurement area, where an entire area of said first optical element couples light to each of said plurality of slits, and having a second area with a receiving window for scattered light from said measurement area and a second optical element receiving said scattered light from said receiving window.

46. A sensor as in claim 45, wherein said optical substrate includes an optical isolator which isolates between said first area and said second area.

47. A sensor as in claim 45, wherein said first optical element is a diffractive lens.

48. A sensor as in claim 45, wherein said optical substrate includes a surface covered with an optical blocking material, and wherein said slits and said window are formed as openings in said optical blocking material.

49. A shear stress sensor, comprising:

an optical substrate, having a first area with a first optical element and a plurality of slits which in combination with said first optical element forms linearly diverging fringes over a measurement area, and having a second area with a receiving window receiving scattered light from two different locations in said measurement area and second and third optical elements receiving said scattered light from said respective two different locations.

50. A sensor as in claim 49, further comprising an optical receiver, receiving said scattered light from said second and third optical elements.

51. A sensor as in claim 50, further comprising a processor, which measures flow velocity at two points to determine said shear stress.

52. A sensor as in claim 51, further comprising an optical isolator which isolates between said first area and said second area.

53. A sensor as in claim 49, wherein said first, second and third optical elements are diffractive optical element.

* * * * *